(12) United States Patent
Cabiri et al.

(10) Patent No.: US 7,087,011 B2
(45) Date of Patent: Aug. 8, 2006

(54) GASTROINTESTINAL SYSTEM WITH TRACTION MEMBER

(75) Inventors: Oz Cabiri, Macabim (IL); Boris Degtiar, Modi'in (IL); Eran Shor, Morhav Bitzaron (IL); Yosef Gross, Morhav Mazor (IL); Benad Goldwasser, Tel Aviv (IL)

(73) Assignee: GI View Ltd., Ramat Gan (IL)

( * ) Notice: Subject to any disclaimer, the term of this patent is extended or adjusted under 35 U.S.C. 154(b) by 240 days.

(21) Appl. No.: 10/747,649

(22) Filed: Dec. 30, 2003

(65) Prior Publication Data

US 2005/0154278 A1    Jul. 14, 2005

(51) Int. Cl.
*A61B 1/00* (2006.01)

(52) U.S. Cl. .................. 600/114; 606/1; 606/108; 604/95.01

(58) Field of Classification Search ........... 600/114; 606/1, 108; 604/95.01
See application file for complete search history.

(56) References Cited

U.S. PATENT DOCUMENTS

| | | |
|---|---|---|
| 4,040,413 A | 8/1977 | Ohshiro |
| 4,066,070 A | 1/1978 | Utsugi |
| 4,077,610 A | 3/1978 | Masuda |
| 4,148,307 A | 4/1979 | Utsugi |
| 4,176,662 A | 12/1979 | Frazer |
| 4,403,985 A | 9/1983 | Boretos |
| 4,530,698 A | 7/1985 | Goldstein et al. |
| 4,561,427 A | 12/1985 | Takada |
| 4,690,131 A | 9/1987 | Lyddy et al. |
| 4,838,859 A | 6/1989 | Strassmann |
| 4,971,034 A | 11/1990 | Doi et al. |
| 4,976,524 A | 12/1990 | Chiba |
| 5,259,364 A | 11/1993 | Bob et al. |
| 5,337,732 A | 8/1994 | Grundfest et al. |
| 5,395,332 A | 3/1995 | Ressemann et al. |
| 5,398,670 A | 3/1995 | Ortiz et al. |
| 5,571,114 A | 11/1996 | Devanaboyina |
| 5,586,968 A * | 12/1996 | Grundl et al. .............. 600/114 |
| 5,604,531 A | 2/1997 | Iddan et al. |
| 5,662,587 A | 9/1997 | Grundfest et al. |
| 5,863,284 A | 1/1999 | Klein |
| 5,879,325 A | 3/1999 | Lindstrom et al. |
| 5,906,591 A | 5/1999 | Dario et al. |
| 5,910,105 A | 6/1999 | Swain et al. |
| 5,941,815 A | 8/1999 | Chang |
| 5,984,860 A | 11/1999 | Shan |
| 6,007,482 A | 12/1999 | Madni et al. |
| 6,028,719 A | 2/2000 | Beckstead et al. |
| 6,071,234 A | 6/2000 | Takada |

(Continued)

FOREIGN PATENT DOCUMENTS

EP    0267446    5/1988

(Continued)

*Primary Examiner*—Linda C. M. Dvorak
*Assistant Examiner*—Matthew J. Kasztejna
(74) *Attorney, Agent, or Firm*—Hoffman, Wasson & Gitler, P.C.

(57) ABSTRACT

A gastrointestinal system including a carrier including an actuator in operative communication with at least one traction member, the actuator moving the at least one traction member relative to the carrier, wherein the at least one traction member is movably supported across supports extending from the carrier, and wherein a portion of the at least one traction member between the supports is sufficiently compliant so as to deform in conformance with a shape of a gastrointestinal tract during traction therealong.

7 Claims, 5 Drawing Sheets

U.S. PATENT DOCUMENTS

| | | | |
|---|---|---|---|
| 6,157,018 A | 12/2000 | Ishiguro et al. | |
| 6,315,713 B1* | 11/2001 | Takada | 600/114 |
| 6,332,865 B1 | 12/2001 | Borody et al. | |
| 6,333,826 B1 | 12/2001 | Charles | |
| 6,341,044 B1 | 1/2002 | Driscoll, Jr. et al. | |
| 6,356,296 B1 | 3/2002 | Driscoll, Jr. et al. | |
| 6,373,642 B1 | 4/2002 | Wallerstein et al. | |
| 6,388,820 B1 | 5/2002 | Wallerstein et al. | |
| 6,424,377 B1 | 7/2002 | Driscoll, Jr. et al. | |
| 6,449,103 B1 | 9/2002 | Charles | |
| 6,459,451 B1 | 10/2002 | Driscoll, Jr. et al. | |
| 6,485,409 B1 | 11/2002 | Voloshin et al. | |
| 6,493,032 B1 | 12/2002 | Wallerstein et al. | |
| 6,503,192 B1 | 1/2003 | Ouchi | |
| 6,517,477 B1 | 2/2003 | Wendlandt | |
| 6,527,705 B1 | 3/2003 | Ouchi | |
| 6,537,206 B1* | 3/2003 | Takada | 600/114 |
| 6,597,520 B1 | 7/2003 | Wallerstein et al. | |
| 6,611,282 B1 | 8/2003 | Trubko et al. | |
| 6,648,814 B1* | 11/2003 | Kim et al. | 600/114 |
| 6,682,479 B1 | 1/2004 | Takahashi et al. | |
| 6,695,771 B1 | 2/2004 | Takada | |
| 6,702,734 B1 | 3/2004 | Kim et al. | |
| 6,702,735 B1 | 3/2004 | Kelly | |
| 6,704,148 B1 | 3/2004 | Kumata | |
| 6,709,388 B1 | 3/2004 | Mosse et al. | |
| 6,764,441 B1 | 7/2004 | Chiel et al. | |
| 6,786,864 B1 | 9/2004 | Matsuura et al. | |
| 6,800,056 B1 | 10/2004 | Tartaglia et al. | |
| 6,814,728 B1 | 11/2004 | Ouchi | |
| 6,824,510 B1* | 11/2004 | Kim et al. | 600/114 |
| 6,827,718 B1 | 12/2004 | Hutchins et al. | |
| 6,837,846 B1 | 1/2005 | Jaffe et al. | |
| 6,866,626 B1 | 3/2005 | Long et al. | |
| 6,869,393 B1 | 3/2005 | Butler | |
| 6,911,005 B1 | 6/2005 | Ouchi et al. | |
| 2002/0012059 A1 | 1/2002 | Wallerstein et al. | |
| 2002/0107478 A1 | 8/2002 | Wendlandt | |
| 2002/0109772 A1 | 8/2002 | Kuriyama et al. | |
| 2002/0109773 A1 | 8/2002 | Kuriyama et al. | |
| 2003/0000526 A1 | 1/2003 | Gobel | |
| 2003/0074015 A1 | 4/2003 | Nakao | |
| 2003/0083547 A1 | 5/2003 | Hamilton et al. | |
| 2003/0105386 A1 | 6/2003 | Voloshin et al. | |
| 2003/0168068 A1 | 9/2003 | Poole et al. | |
| 2003/0181788 A1* | 9/2003 | Yokoi et al. | 600/160 |
| 2003/0191369 A1 | 10/2003 | Arai et al. | |
| 2003/0208219 A1 | 11/2003 | Aznoian et al. | |
| 2003/0225433 A1 | 12/2003 | Nakao | |
| 2004/0004836 A1 | 1/2004 | Dubuc | |
| 2004/0111010 A1 | 6/2004 | Nishiie | |
| 2004/0199087 A1 | 10/2004 | Swain et al. | |
| 2004/0199088 A1 | 10/2004 | Bakos et al. | |
| 2004/0199196 A1 | 10/2004 | Ravo | |
| 2004/0204702 A1 | 10/2004 | Ziegler et al. | |
| 2004/0249247 A1 | 12/2004 | Iddan | |
| 2004/0260150 A1 | 12/2004 | Bernstein | |
| 2005/0038317 A1 | 2/2005 | Ratnakar | |
| 2005/0095200 A1 | 5/2005 | Schwarzberg | |

FOREIGN PATENT DOCUMENTS

| | | |
|---|---|---|
| FR | 1465723 | 3/1967 |
| WO | WO 01/68540 | 9/2001 |
| WO | WO 02/059676 | 8/2002 |
| WO | WO 02/075348 | 9/2002 |
| WO | WO 03/026272 | 3/2003 |
| WO | WO 03/045487 | 6/2003 |
| WO | WO 03/046830 | 6/2003 |
| WO | WO 03/053225 | 7/2003 |
| WO | WO 04/010858 | 2/2004 |
| WO | WO 04/069057 | 8/2004 |

* cited by examiner

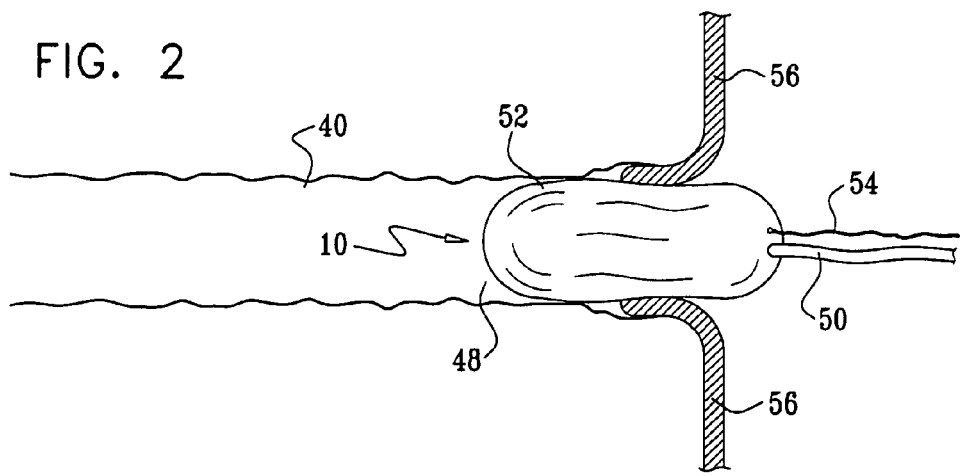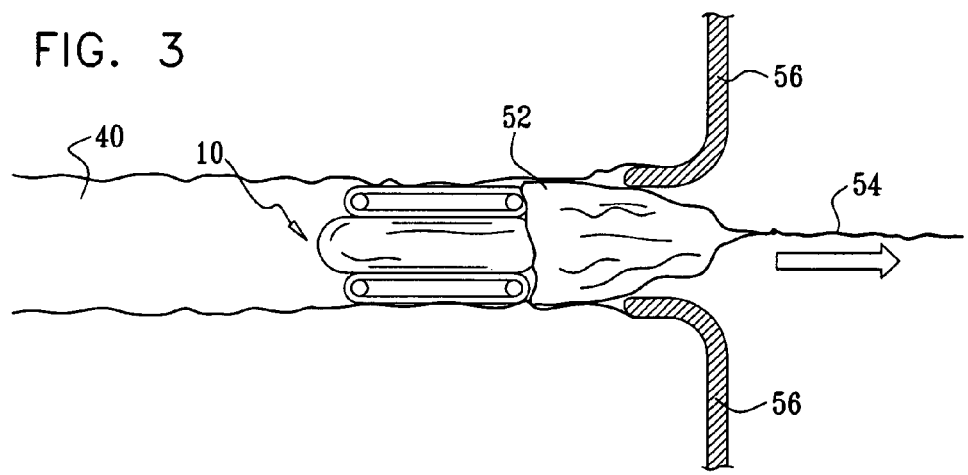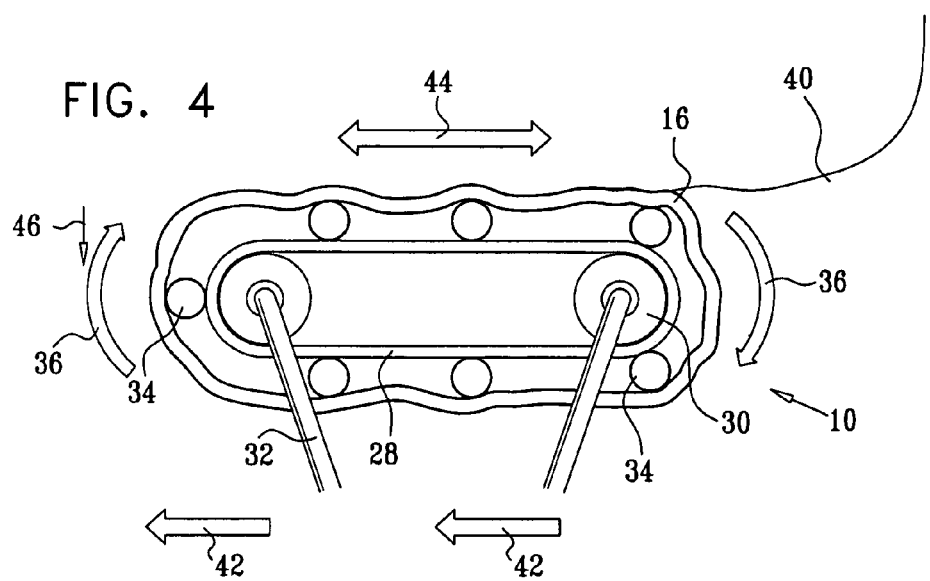

GASTROINTESTINAL SYSTEM WITH TRACTION MEMBER

FIELD OF THE INVENTION

The present invention relates generally to medical imaging, diagnostic and therapeutic systems, and particularly to a self-propelled imaging, diagnostic and therapeutic system that moves along a gastrointestinal (GI) tract by traction.

BACKGROUND OF THE INVENTION

Many imaging devices are known for producing medical images of body lumens, such as the gastrointestinal (GI) tract. For example, endoscopy is widely used for observing, photographing tissue, and taking specimens from lesions and the like. In a conventional method of examining a colon using an endoscope, for example, the endoscope is typically manually inserted into the colon. In this manual technique, patients may often complain of abdominal pain and distention because the colon is extended or excessively dilated, thereby necessitating stopping the endoscopic procedure. Furthermore, it is not unusual for the colon to bleed and be accidentally perforated. Insertion of an endoscope through the sigmoid colon and into the descending colon, or through the splenic flexure, the transverse colon, the hepatic flexure or parts affected by previous operations may also be accompanied with difficulty. Because of these reasons, a colonoscopy is typically performed by a relatively few number of skilled practitioners, and the rate of patient pain and discomfort is high.

SUMMARY OF THE INVENTION

The present invention seeks to provide an improved gastrointestinal system which is self-propelled, suitable for imaging body lumens, such as the gastrointestinal (GI) tract, as is described in detail further hereinbelow. The imaging system of the invention may be sterile and disposable, and may be manufactured at very low cost. The system may have very low friction and provide maximum comfort and flexibility. The system provides excellent visibility and its motion may be controlled by its own propulsion and/or may be externally controlled by an operator or some remote device, or any combination thereof. The system may successfully track along the colon even up to the cecum without blockage and slippage.

There is thus provided in accordance with an embodiment of the present invention a gastrointestinal system including a carrier including an actuator in operative communication with at least one traction member, the actuator moving the at least one traction member relative to the carrier, wherein the at least one traction member is movably supported across supports extending from the carrier, and wherein a portion of the at least one traction member between the supports is sufficiently compliant so as to deform in conformance with a shape of a gastrointestinal tract during traction therealong.

The gastrointestinal system may include one or more of the following features. For example, the traction members may be arranged for rotation about a pulley system. The pulley system may be coupled to the actuator by a gear train. The pulley system may include a belt placed around pulley wheels, wherein the traction member may be spaced from and connected to the belt by spacers. The traction member may be more compliant than the belt. An imaging device, diagnostic device and/or therapeutic device may be disposed in the carrier. The carrier may be at least partially disposed in a removable sheath. A protective funnel may be provided for introducing/extracting the gastrointestinal system in/from a body lumen.

BRIEF DESCRIPTION OF THE DRAWINGS

The present invention will be understood and appreciated more fully from the following detailed description taken in conjunction with the drawings in which:

FIG. 2 is a simplified side view illustration of introducing the gastrointestinal system of FIG. 1 into a rectum, wherein the gastrointestinal system is initially disposed in a sheath;

FIG. 3 is a simplified side view illustration of removing the sheath to expose the gastrointestinal system;

FIG. 4 is a simplified side view illustration of one of the traction members tracking along the gastrointestinal tract, in accordance with an embodiment of the present invention;

DETAILED DESCRIPTION OF THE PREFERRED EMBODIMENT

Figure 1:
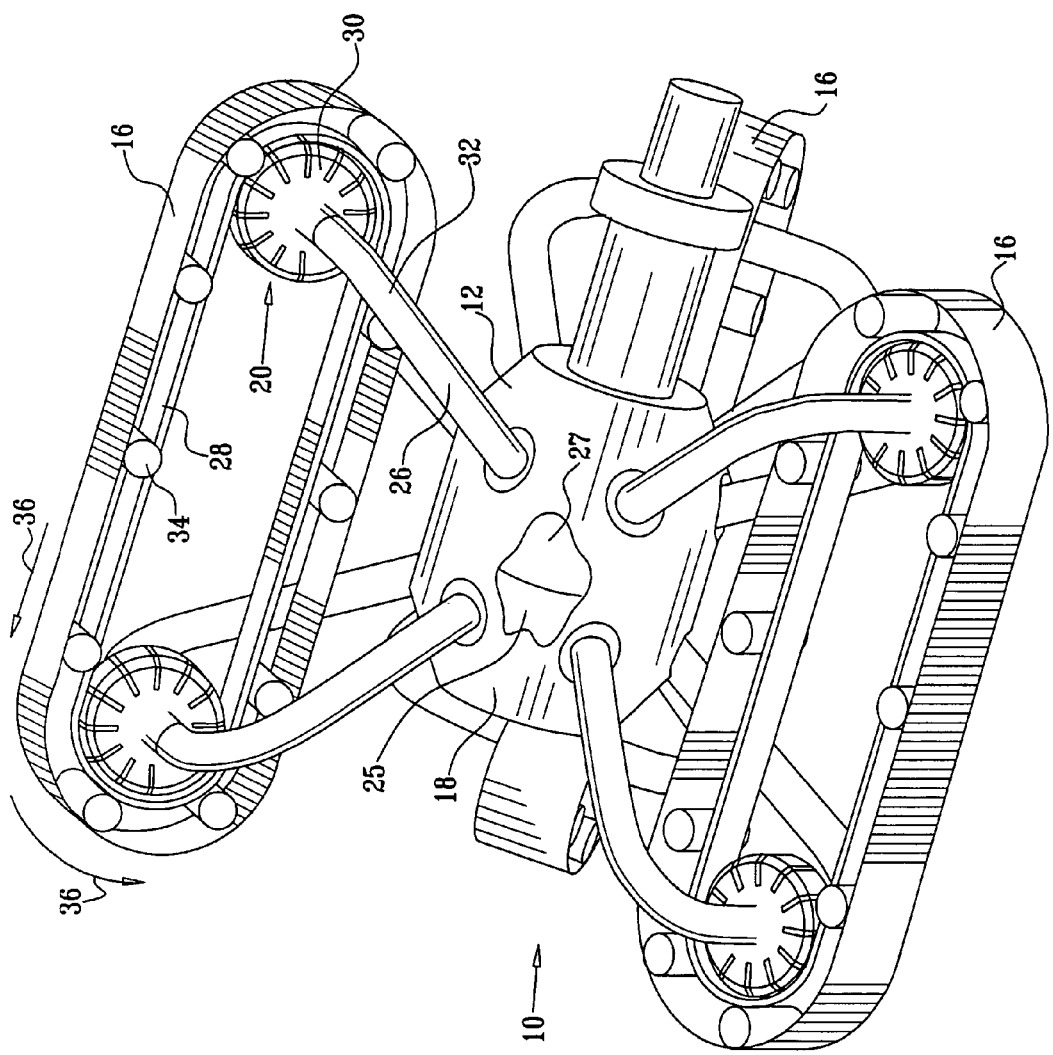
FIG. 1 is a simplified pictorial illustration of a gastrointestinal system, constructed and operative in accordance with an embodiment of the present invention, comprising traction members extending from a carrier.

Reference is now made to FIG. 1, which illustrates a gastrointestinal system 10, constructed and operative in accordance with an embodiment of the present invention.

Gastrointestinal system 10 may comprise a carrier 12 that includes an actuator 14 (seen in FIG. 5 or FIG. 6) in operative communication with one or more traction members 16. In the illustrated embodiment, carrier 12 may include a barrel-shaped body with an imaging device 18 disposed therein. (It is noted that the invention is not limited in any way to this configuration.) Imaging device 18 may comprise a camera or CCD, in which case the body of carrier 12 in the area of imaging device 18 is preferably transparent to facilitate capture of images. Imaging device 18 may alternatively comprise other devices, such as but not limited to, an x-ray imaging device.

Figure 5:
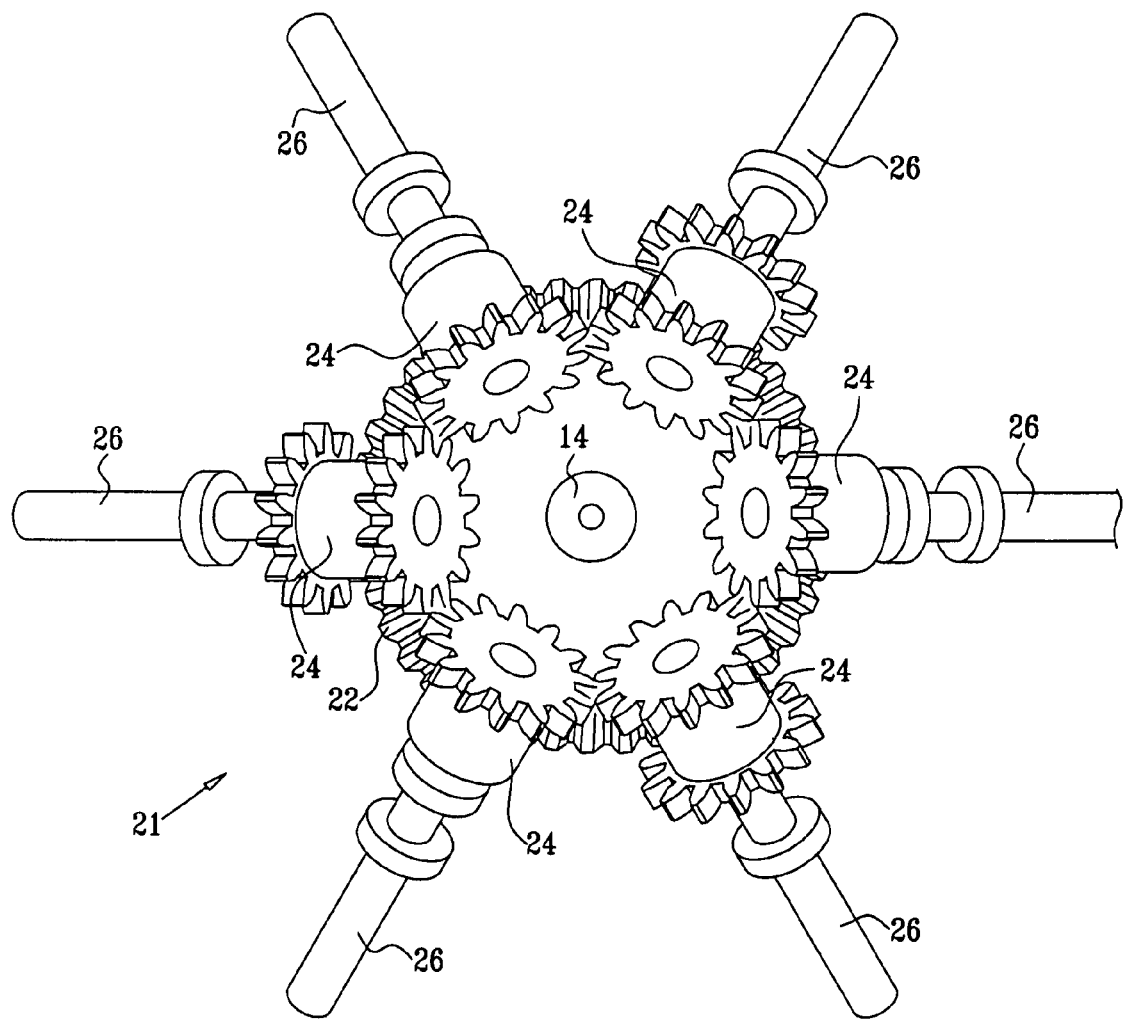
FIG. 5 is a simplified pictorial illustration of a portion of an actuator that moves the traction members so as to propel the gastrointestinal system along the gastrointestinal tract, constructed and operative in accordance with an embodiment of the present invention.

Additionally or alternatively, a diagnostic device 25 and/or therapeutic device 27 may be disposed in carrier 12, for example, without limitation, an iontophoresis drug delivery device (e.g., including an active (drug delivery) electrode with a reservoir of a drug to be administered, and a dispersive electrode connected to an iontophoretic current generator that produces a controlled, direct current stimulus for iontophoretic delivery of the drug), an injection device for injection of a substance (e.g., a miniature hypodermic needle with a syringe containing a substance to be injected), a photodynamic therapy/diagnosis device (e.g., an LED-based light infusion device), a hyperthermic therapy/diagnosis device (e.g., miniature high frequency ultrashort wave electrodes), an ultrasonic therapy/diagnosis device (e.g., miniature ultrasound transducer). Another gastrointestinal tool may include a dye applicator, which may be used to coat, paint, spray or otherwise apply a color, pigment, dye or other highlighting substance on the inner walls of the GI tract. In this manner, polyps or other growths or anomalies may be highlighted so that they are more easily discerned and imaged by the colonoscope. This may also aid in pattern recognition by the colonoscope. It is also noted that certain polyps or other growths may react differently to the addition of the dye, such as in terms of color change, absorption, etc., and the reaction of the growth may be correlated to its probability of turning into a cancerous growth. Any number of traction members 16 may be provided, such as three in the illustrated embodiment. The traction member 16 may include a compliant belt (of any width and size) arranged for rotation about a pulley system 20. Actuator 14 may comprise a servomotor, for example, coupled to pulley system 20 by a gear train 21. For example, as seen in FIG. 5, the gear train 21 may include a central beveled gear 22 to which are meshed a plurality of spur gears 24 mounted on shafts 26. Actuator 14 may rotate the central beveled gear 22, which in turn causes rotation of the spur gears 24 and shafts 26. The shafts 26 and/or any other support elements of the traction members 16 may be flexible or spring-biased so that when the gastrointestinal system 10 is deployed in the GI tract, the traction members 16 are urged against the inner walls of the GI tract.

Figure 6:
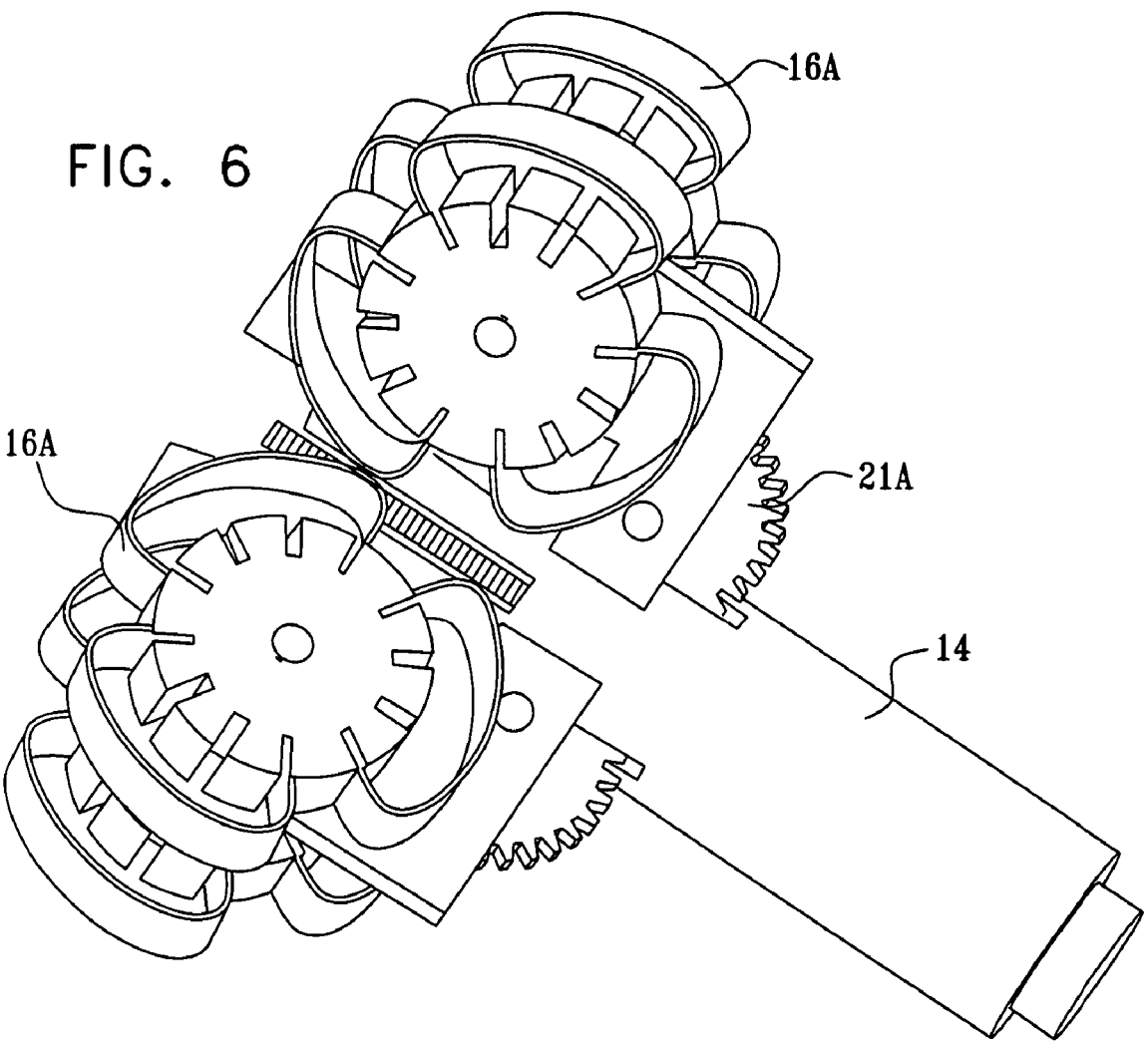
FIG. 6 is a simplified pictorial illustration of an actuator that moves the traction members, constructed and operative in accordance with another embodiment of the present invention.

FIG. 6 illustrates an alternative arrangement of the actuator 14 coupled to traction members 16A with another gear train 21A. It is appreciated that these are just two examples of embodiments of the actuator and traction members, and many other configurations and linkages are possible within the scope of the invention.

Referring again to FIG. 1, the pulley system 20 may comprise a belt 28 placed around pulley wheels 30. The pulley wheels 30 may be mounted for rotation on ends of shafts 26 by any suitable connection or linkage 32. The traction member 16 may be spaced from and connected to belt 28 by spacers 34. The traction member 16 may be more compliant than belt 28. For example, traction member 16 may be constructed of silicone rubber or some other medically safe elastomer, and belt 28 may be constructed of a stiffer medically safe elastomer, such as polyurethane.

Reference is now made additionally to FIG. 4. The actuator 14 moves the traction members 16 relative to carrier 12, as indicated by arrows 36. The traction members 16 are movably supported across supports extending from carrier 12, wherein in the illustrated embodiment, the supports are the pulley system 20 with its spacers 34. A portion of the traction member 16 between the supports (e.g., between spacers 34) is sufficiently compliant so as to deform in conformance with a shape of the gastrointestinal tract 40 during traction therealong (in the direction of arrows 42). "Traction" of traction member 16 along the GI tract 40 refers to the adhesive force between the traction member 16 and the GI tract 40 that is used to propel the system along the GI tract 40. The compliance and resilience of the traction member 16 may help in advancing the system in the tortuous and flexible passageways of the GI tract 40.

It is noted that the shear adherence of traction member 16 to the GI tract 40 in a direction along a surface of the GI tract 40 (as indicated by arrows 44) is greater than the tensile adherence of traction member 16 to the GI tract 40 in a direction perpendicularly away from the surface of the GI tract 40 (as indicated by arrow 46).

Reference is now made to FIG. 2, which illustrates introducing the gastrointestinal system 10 into a rectum 48. The gastrointestinal system 10 may be mounted on a wire or other slender member 50. Power may be supplied to the gastrointestinal system 10 via slender member 50, such as but not limited to, electrical power (e.g., supplied through wires in slender member 50), tubing connected to a source of positive fluid pressure (e.g., for introducing air or water) or a source of negative fluid pressure (e.g., suction). Alternatively, the gastrointestinal system 10 may comprise its own battery or other power source.

The gastrointestinal system 10 may be initially disposed in a sheath 52 that serves as a protective cover for the gastrointestinal system 10 during insertion in the rectum 48. Sheath 52 may be flexible or rigid. Sheath 52 may be provided with a pull-wire 54 to remove the sheath afterwards (as seen in FIG. 3).

In accordance with another embodiment of the present invention, sheath 52 may alternatively be configured to remain in the anus and simply open to release the gastrointestinal system 10, which exits the sheath 52 and proceeds into the GI tract. After the gastrointestinal system 10 has traveled in the GI tract, the gastrointestinal system 10 may be extracted back into the sheath 52. The sheath 52 may lower the friction of the guidewire against the anus during use of the gastrointestinal system 10. Additionally or alternatively, a protective funnel 56 may be provided for introducing/extracting gastrointestinal system 10 in/from the body lumen (rectum).

Figure 7:
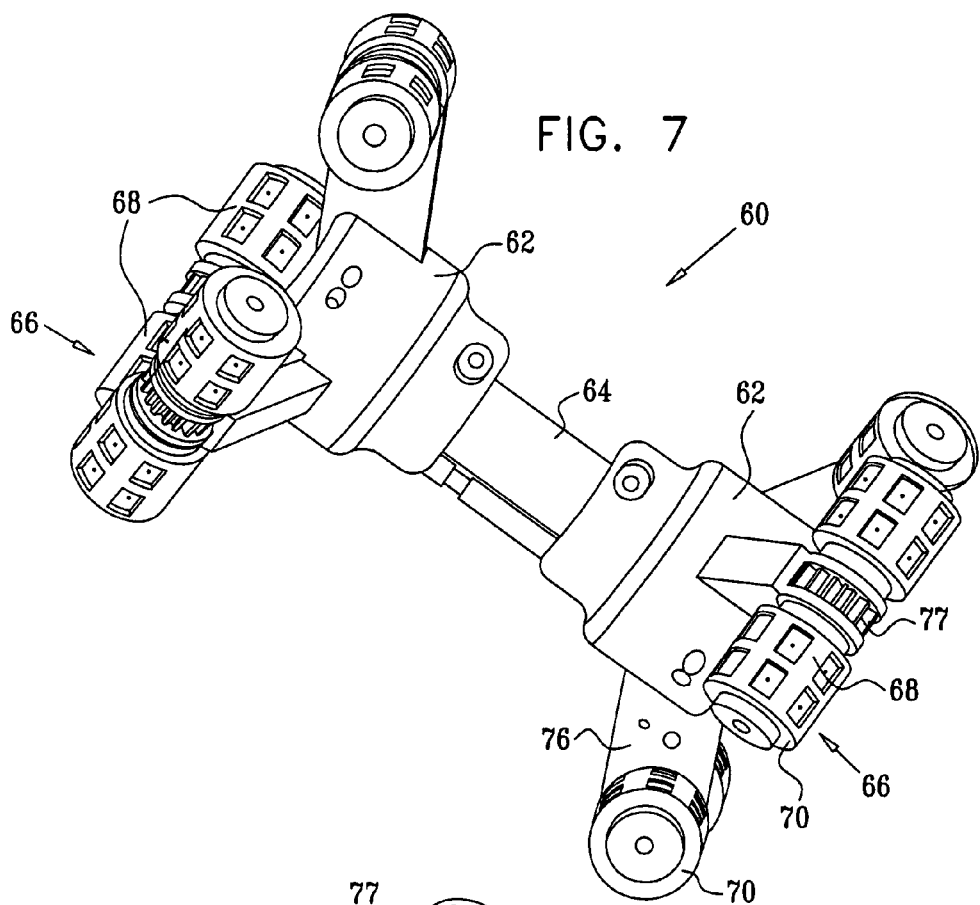
FIG. 7 is a simplified pictorial illustration of a gastrointestinal system, constructed and operative in accordance with another embodiment of the present invention, comprising traction members extending from a carrier.

Reference is now made to FIG. 7, which illustrates a gastrointestinal system 60, constructed and operative in accordance with another embodiment of the present invention.

Gastrointestinal system 60 may comprise a carrier 62 and an actuator 64, which may be constructed in a similar manner as described hereinabove for the gastrointestinal system 10. Thus the detailed description of the carrier and actuator does not need to be repeated. As described before for the gastrointestinal system 10, the gastrointestinal system 60 may include an imaging device disposed therein, diagnostic and/or therapeutic devices and gear trains or other drive system to drive traction members 66.

Figure 8:
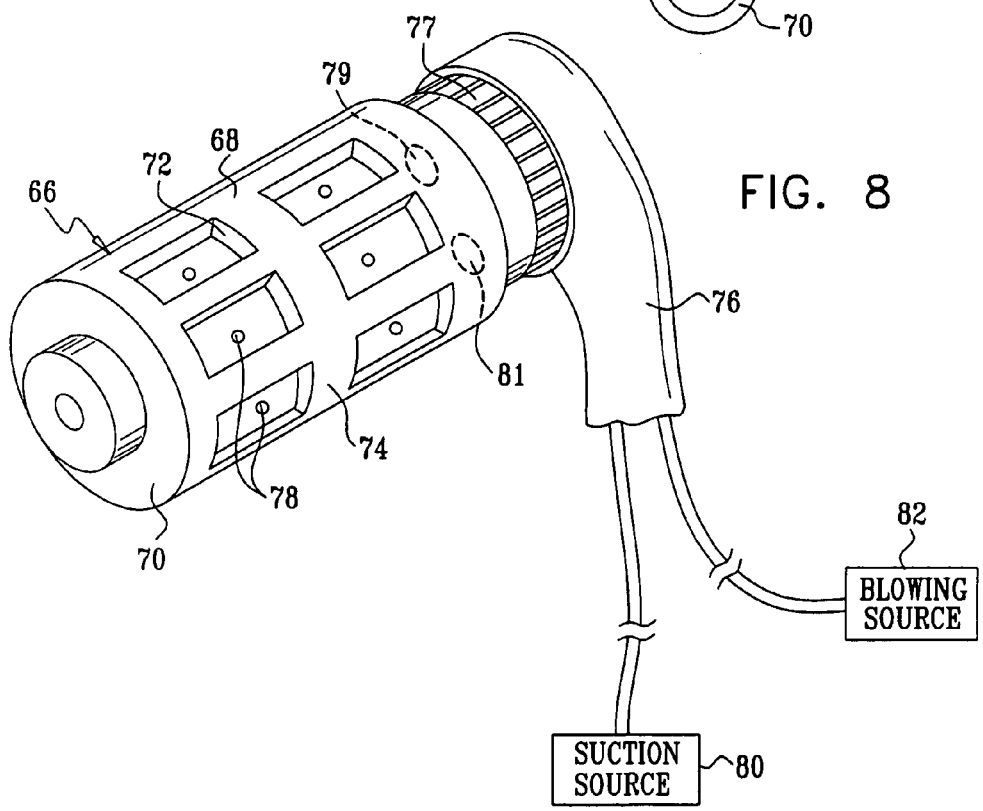
FIG. 8 is a simplified illustration of a roller of the gastrointestinal system of FIG. 7.

In the gastrointestinal system 60, the traction member 66 may include an elastomeric member 68 applied over a roller 70 (shown more in detail in FIG. 8). The elastomeric member 68 may be stretched tightly or loosely over roller 70. Alternatively, the elastomeric member 68 may be coated on roller 70. The elastomeric member 68 may be constructed of silicone rubber or some other medically safe elastomer, for example. Roller 70 may be constructed with a "waffle-like" outer surface, comprising a plurality of indentations 72 separated by walls 74. Roller 70 may be mounted for rotation on an arm 76. Actuator 64 may be connected to roller 70 by a gear train 77 or other linkage. As before, traction member 66 is sufficiently compliant so as to deform in conformance with a shape of the GI tract during traction therealong.

Fluid passages 78 may be built into rollers 70 and arranged for fluid communication (e.g., with the fluid being air) with one or more ports 79 formed in arms 76. One of the ports 79 may be connected to a source of negative pressure (suction), referred to as suction source 80, which may be housed in carrier 62 or which may be external to the gastrointestinal system 10 and connected thereto with appropriate tubing. The suction source 80 may draw a vacuum through port 79 and through fluid passage 78 so as to suck the tissue of the body lumen (e.g., GI tract) against the elastomeric member 68, thereby enhancing the traction of the gastrointestinal system 60 with the body lumen walls.

Additionally or alternatively, another port 81 may be connected to a source of positive pressure (blowing), referred to as blowing source 82, which may be housed in carrier 62 or which may be external to the gastrointestinal system 10 and connected thereto with appropriate tubing. As the roller 70 rotates, it first aligns with the port 79 that is connected to the suction source 80. Continued rolling of the roller 70 results in alignment with the port 81 that is connected to the blowing source 82. The blowing source 82 may force fluid (e.g., air) through port 81 and through fluid passage 78 so as to clean fluid passage 78 from any debris that may have accumulated thereon.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A gastrointestinal system comprising:
    at least one traction member;
    a carrier comprising an actuator in operative communication with said at least one traction member, said actuator moving said at least one traction member relative to said carrier, wherein a portion of said at least one traction member is sufficiently compliant so as to deform in conformance with a shape of a gastrointestinal tract during traction therealong; and
    a pulley system,
    wherein said at least one traction member is arranged for rotation about said pulley system, and
    wherein said pulley system comprises:
    pulley wheels;
    a belt placed around said pulley wheels; and
    spacers, which space said at least one traction member from and connect said at least one traction member to said belt.

2. The gastrointestinal system according to claim 1, wherein said at least one traction member is more compliant than said belt.

3. A gastrointestinal system comprising:
    at least one traction member;
    a carrier comprising an actuator in operative communication with said at least one traction member, said actuator moving said at least one traction member relative to said carrier, wherein a portion of said at least one traction member is sufficiently compliant so as to deform in conformance with a shape of a gastrointestinal tract during traction therealong,
    wherein said at least one traction member comprises: an arm;
    a roller, mounted for rotation on said arm and operatively connected to said actuator; and
    an elastomeric member applied over said roller.

4. The gastrointestinal system according to claim 3, wherein said elastomeric member is stretched over said roller.

5. The gastrointestinal system according to claim 3, wherein said elastomeric member is coated on said roller.

6. The gastrointestinal system according to claim 3, wherein an outer surface of said roller is shaped so as to define a plurality of indentations separated by walls.

7. The gastrointestinal system according to claim 3, wherein said roller is shaped so as to define a fluid passage arranged for fluid communication with at least one port formed in said arm, said port being adapted to be connected to at least one source selected from the group consisting of: a suction source and a blowing source.

* * * * *